United States Patent
Schlereth

(10) Patent No.: US 9,435,767 B2
(45) Date of Patent: Sep. 6, 2016

(54) SENSOR FOR SENSING SUBSTANCES IN AN ENVIRONMENT

(71) Applicant: Syracuse University, Syracuse, NY (US)

(72) Inventor: Fritz H. Schlereth, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 254 days.

(21) Appl. No.: 14/017,841

(22) Filed: Sep. 4, 2013

(65) Prior Publication Data

US 2014/0060191 A1 Mar. 6, 2014

Related U.S. Application Data

(60) Provisional application No. 61/696,389, filed on Sep. 4, 2012.

(51) Int. Cl.
*G01N 29/02* (2006.01)
*G01N 29/44* (2006.01)

(52) U.S. Cl.
CPC ........ *G01N 29/022* (2013.01); *G01N 29/4436* (2013.01)

(58) Field of Classification Search
CPC .................. G01N 29/022; G01N 29/4436
USPC ..................................... 73/579, 580
See application file for complete search history.

(56) References Cited

U.S. PATENT DOCUMENTS

| 4,701,712 A * | 10/1987 | Seeley et al. ............... 324/340 |
| 5,311,152 A * | 5/1994 | Lautzenhiser ............... 332/127 |
| 2002/0094796 A1* | 7/2002 | Woods et al. ............... 455/260 |
| 2003/0001680 A1* | 1/2003 | Knecht et al. ............... 331/18 |
| 2003/0137361 A1* | 7/2003 | Knecht et al. ............... 331/176 |
| 2010/0236331 A1* | 9/2010 | Wakamatsu ............... 73/651 |
| 2012/0152018 A1* | 6/2012 | Kudo et al. ............... 73/384 |

OTHER PUBLICATIONS

Steven G. Haupt et al., Applicability of Portable Explosive Detection Devices in Transit Environments, 2004, TCRP Report 86, Public Transportation Security, vol. 6, 44 pages.

Existing and Potential Standoff Explosives Detection Techniques, 2004, National Research Council of the National Academies, 148 pages.

Lisa Thiesan et al., Survey of Commercially Available Explosives Detection Technologies and Equipment 2004, Nov. 2004, The National Law Enforcement and Correction Technology Center, 97 pages.

(Continued)

*Primary Examiner* — J M Saint Surin
(74) *Attorney, Agent, or Firm* — Heslin Rothenberg Farley & Mesiti P.C.; George Blasiak

(57) ABSTRACT

There is set forth herein a sensor for sensing of substances. The sensor can include a sensing crystal oscillator and a reference crystal oscillator. The sensing crystal oscillator and the reference crystal oscillator can be arranged in a phase locked loop so that the oscillators oscillate at a common frequency. The sensor can be configured so that there is a baseline phase differential between the oscillation frequencies of the sensing crystal oscillator and the reference crystal oscillator. Detectable substances accumulating on the sensing crystal oscillator will induce a phase shift between output frequencies of the reference oscillator and the sensing crystal oscillator to allow for highly sensitive sensing of substances in small concentrations.

20 Claims, 4 Drawing Sheets

(56) References Cited

OTHER PUBLICATIONS

Neena A. Gilda et al., Piezoresistive 6-MNA Coated Microcantilevers with Signal Conditioning Circuits for Electronic Nose, Nov. 2011, IEEE Asian Solid-State Circuits Conference, pp. 121-124.

Simon Clavaguera et al., Comparison of Fluorescence and QCM Technologies: Example of Explosives Detection with a π-Conjugated Thin Film, 2010, Science Direct, Elsevier, Talanta, pp. 1397-1402.

F. Parret et al., Detection of Explosives Vapors with a Portable Detector Based on Quartz-Crystal Microbalance, Oct. 2007, IEEE Sensors 2007 Conference, pp. 248-251.

\* cited by examiner

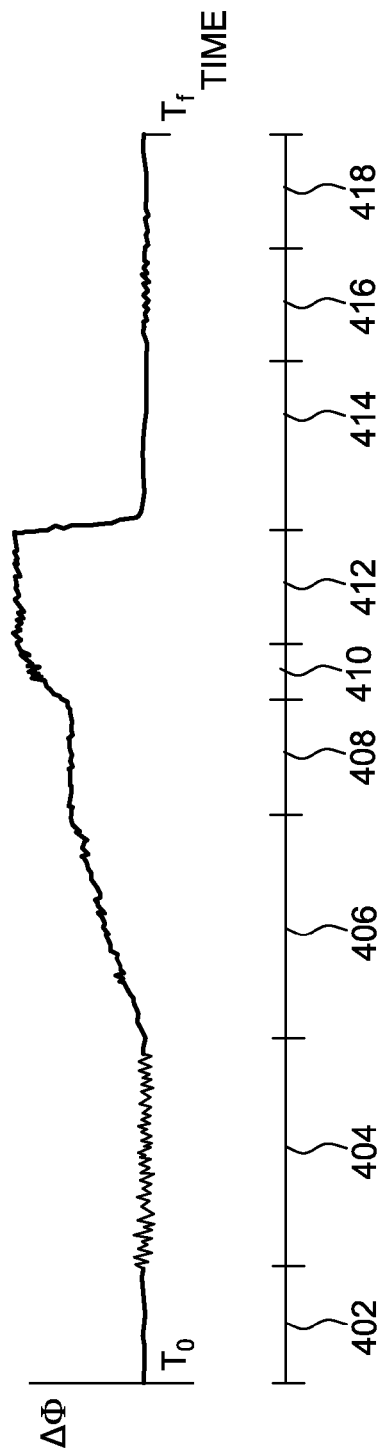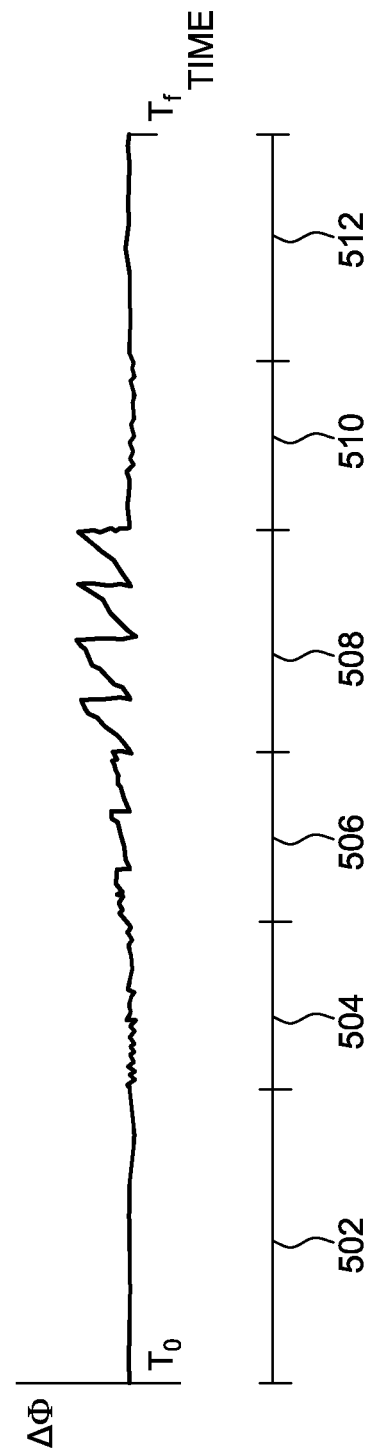

SENSOR FOR SENSING SUBSTANCES IN AN ENVIRONMENT

CROSS REFERENCE TO RELATED APPLICATIONS

This application is a nonprovisional of U.S. Patent Application No. 61/696,389 filed Sep. 4, 2012 entitled, "SENSOR FOR SENSING SUBSTANCES IN AN ENVIRONMENT." The above application is incorporated herein by reference in its entirety.

FIELD OF THE INVENTION

The invention relates to sensors in general and specifically to a sensor comprising a crystal oscillator.

BACKGROUND OF THE INVENTION

Quartz crystal oscillator sensors have long been used to measure mass, e.g., in semiconductor fabrication environments. Operation of such sensors is based on the frequency of oscillation of an oscillating quartz crystal oscillator as a function of the mass of the crystal. Depositing material on a face of the crystal changes its mass and by measuring the frequency it is possible to measure mass of a material deposited.

SUMMARY OF THE INVENTION

There is set forth herein a sensor for sensing of substances. The sensor can include a sensing crystal oscillator and a reference crystal oscillator. The sensing crystal oscillator and the reference crystal oscillator can be arranged in a phase locked loop so that the oscillators oscillate at a common frequency. The sensor can be configured so that there is a baseline phase differential between the oscillation frequencies of the sensing crystal oscillator and the reference crystal oscillator. Detectable substances accumulating on the sensing crystal oscillator will induce a phase shift between output frequencies of the reference oscillator and the sensing crystal oscillator to allow for highly sensitive sensing of substances in small concentrations. A phase analyzer comprising a phase comparator can be disposed at the output of the first crystal oscillator and the second crystal oscillator. The output of the phase analyzer can be indicative of a detectable substance. The output of the phase analyzer can be monitored for detecting a presence of a substance. When a substance accumulates on the sensing crystal oscillator, a phase shift in relative outputs of the sensing crystal oscillator and the reference oscillator will be realized.

BRIEF DESCRIPTION OF DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIG. 4 is an exemplary DSP output in a first embodiment of a sensor.
FIG. 5 is an exemplary DSP output in a second embodiment of a sensor.

DETAILED DESCRIPTION OF THE INVENTION

Figure 1:
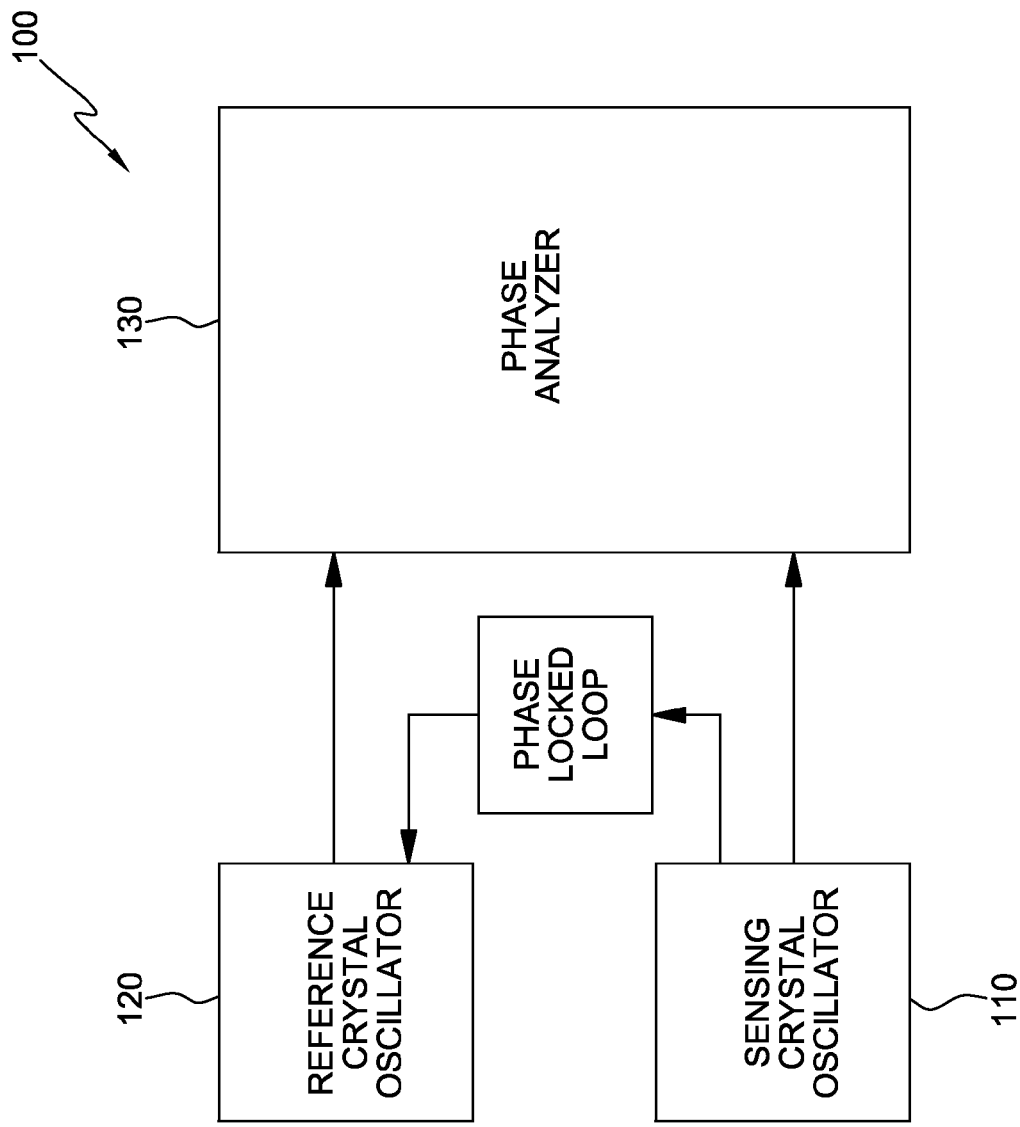
FIG. 1 is a block diagram of a sensor.
Figure 2:
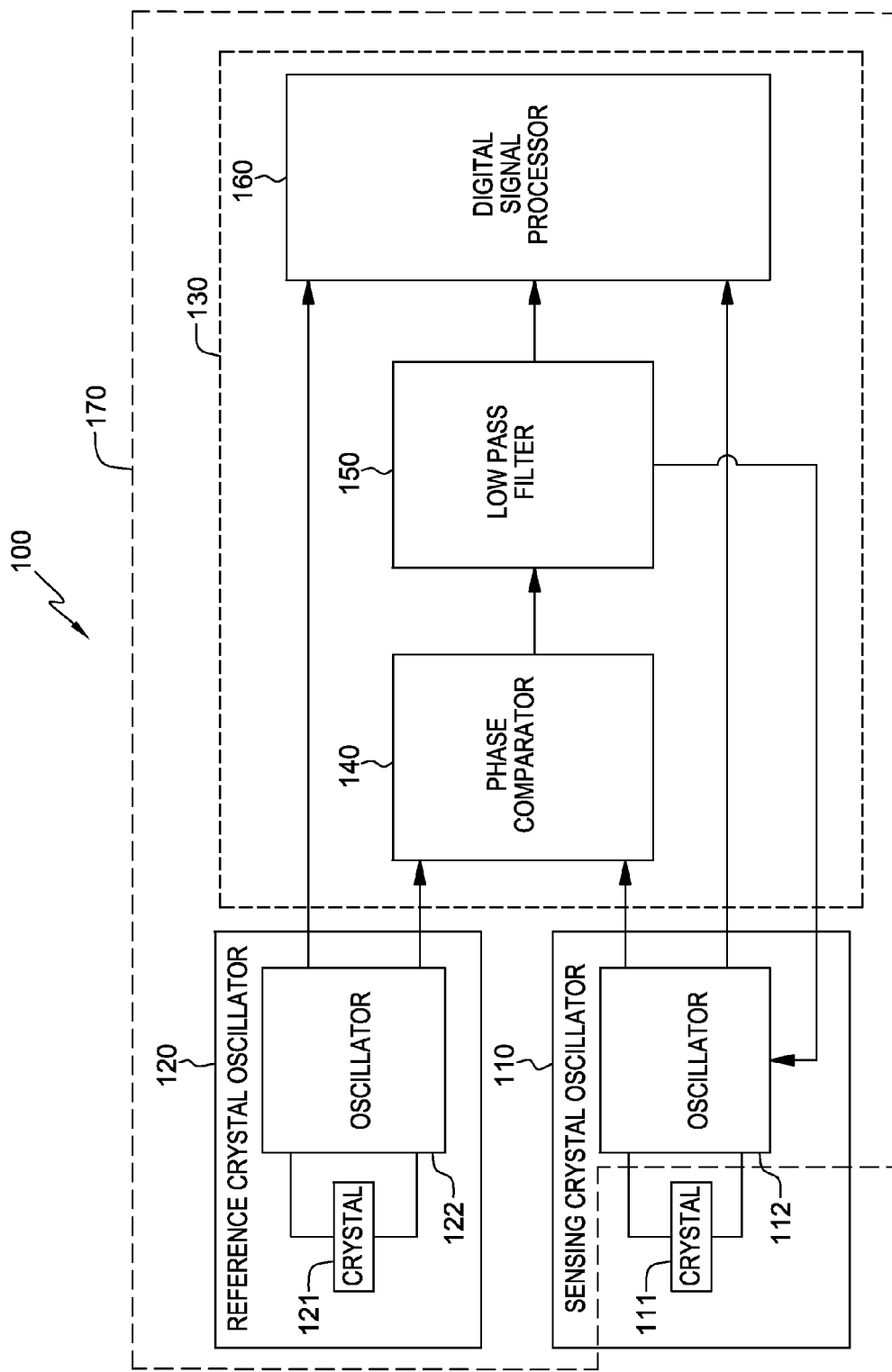
FIG. 2 is a further detailed exemplary block diagram of a sensor.

There is set forth herein with reference to FIGS. 1 and 2 a sensor 100 for sensing of substances in an environment. The sensor 100 can include a sensing crystal oscillator 110 and a reference crystal oscillator 120. The sensing crystal oscillator 110 and the reference crystal oscillator 120 can be arranged in a phase locked loop so that the oscillators oscillate and output signals that are at a common frequency. The sensor can be configured so that there is a baseline phase differential between the oscillation frequencies of the sensing crystal oscillator 110 and the reference crystal oscillator 120. Detectable substances accumulating on the sensing crystal oscillator 110 can induce a phase shift between output signal frequencies of the sensing crystal oscillator 110 and the reference crystal oscillator 120 to allow for highly sensitive sensing of substances in small concentrations. A phase analyzer 130 can be disposed at the output of the first crystal oscillator and the second crystal oscillator. An output of phase analyzer 130 can be responsive to a change in phase differential (a phase shift) in the outputs of reference crystal oscillator 120 and reference crystal oscillator 120. When a substance accumulates on the sensing crystal oscillator 110 an output of phase analyzer 130 can indicate there being a phase shift in the outputs of reference crystal oscillator 120. An output of phase analyzer 130 indicating a phase shift the outputs of sensing crystal oscillator 110 and reference crystal oscillator 120 is indicative of there being a substance in an environment in which sensor 100 is disposed. In one embodiment, sensor 100 can be used to detect contaminants in indoor and outdoor environments that effect human health and productivity. In one embodiment, sensor 100 can be used to detect explosives in an environment.

In one embodiment, sensing crystal oscillator 110 and reference crystal oscillator 120 can be selected to be quartz crystal oscillators operating at a frequency of about 6 MHz. In one embodiment, as indicated by dashed line 170 illustrated with reference to FIG. 2, sensor 100 is packaged in a package (represented by dashed line) so that sensing crystal 111 of sensing crystal oscillator 110 is exposed to an environment subject to sensing and remaining components of sensor 100, including reference crystal oscillator 120, are not exposed to an environment subject to sensing. With reference to FIG. 2, it is illustrated that sensing crystal oscillator 110 can comprise a crystal 111 and an oscillator 112. Further, with reference to FIG. 2 it is shown that reference crystal oscillator 120 can comprise a crystal 121 and an oscillator 122.

Provided as described, sensor 100 is capable of making highly precise measurements of substances in an environment. With sensing crystal oscillator 110 and reference crystal oscillator 120 arranged in a phase locked loop small changes in frequency of the oscillator are realized as detectable changes in phase as output by phase analyzer 130. A change in phase occurs because the phase lock system requires a change in phase to maintain a frequency lock. A change in phase by a small number of degrees is easily detected with use of phase analyzer 130. With sensor 100 configured as set forth herein, a period of oscillation of sensing crystal oscillator 110 can be proportional to a mass of molecules adhering to a surface of sensing crystal oscillator 110. Without a substance accumulated on sensing crystal oscillator 110 a phase differential between sensing crystal oscillator 110 and reference crystal oscillator 120 can be maintained at a constant phase, changing only by a random noise factor, known as noise jutter. In the event a substance is accumulated on sensing crystal oscillator 110 the phase differential between an output signal of sensing crystal oscillator 110 and reference crystal oscillator 120 can change. For encouraging accumulation of a substance on sensing crystal oscillator 110, sensing crystal oscillator 110 can be coated with an attractant. In one specific example, sensor 100 can be utilized to measure minute traces of explosive molecules, e.g. TNT, RDA and sensing crystal oscillator 110 can be coated with 6-MNA, mercaptonicotinic acid.

In the embodiment of FIG. 2, phase analyzer 130 comprises a phase comparator 140 a low pass filter 150 and a digital signal processor DSP 160. In one embodiment, phase analyzer 130 can include a phase comparator 140 coupled to voltage outputs of sensing crystal oscillator 110 and reference crystal oscillator 120. The output of the phase comparator 140 is indicative of a detectable substance. The output of the phase comparator 140 can be monitored for detecting a presence of a substance.

Figure 3:
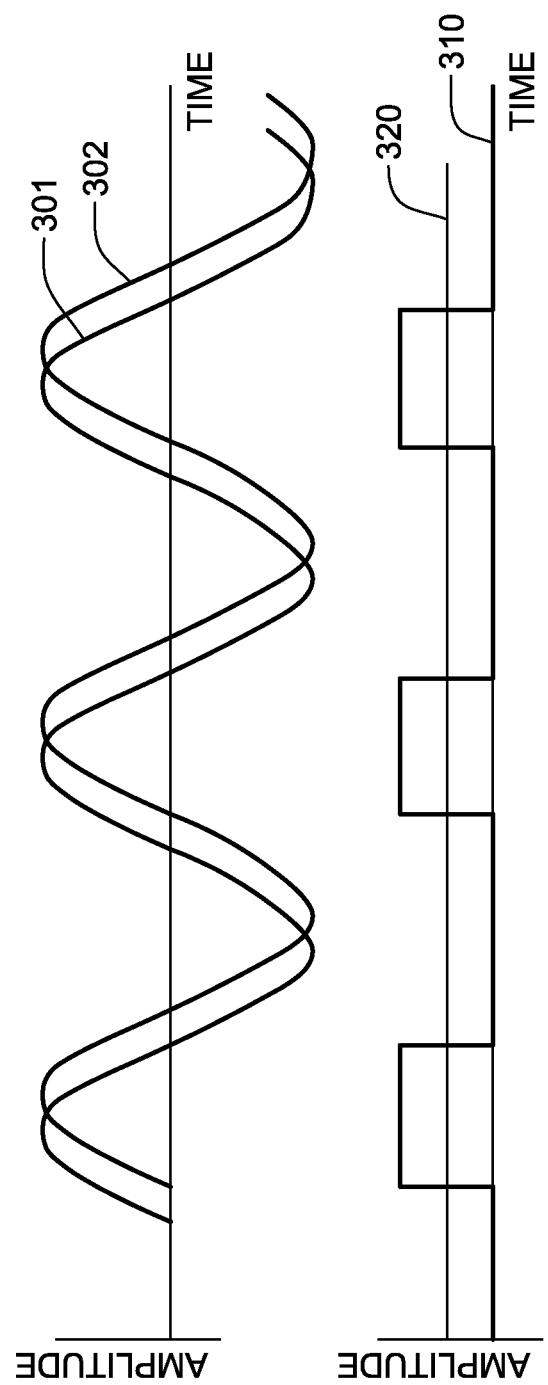
FIG. 3 is an exemplary output of a phase comparator.

An output of an exemplary phase comparator 140 is shown in FIG. 3. Phase comparator 140, as illustrated in FIG. 3 can output a square wave 310 of pre-set amplitude when both an amplitude of output signal 301 of sensing crystal oscillator 110 and an amplitude of output signal 302 of reference crystal oscillator 120 are positive. In such manner a length of pulses (e.g., square wave or other shape) will increase or decrease when there is a phase shift (a change in a phase differential between output signals of sensing crystal oscillator 110 and reference crystal oscillator 120). There can also be output by comparator 140 a DC phase comparator tracking signal 320 which tracks the average amplitude of square wave signal 310 over time. In one embodiment signal 320 tracks phase changes for a time that sensor 100 remains "on." In one embodiment, signal 320 is periodically re-set to a baseline value during an on time of sensor 100.

Without any substance accumulated on sensing crystal oscillator 110 an output of phase comparator tracking signal 320 tracking changing a phase differential between the output of sensing crystal oscillator 110 and reference crystal oscillator 120 can be expected to exhibit random noise jitter, repeatedly falling below or rising above a baseline value over time, indicating a jitter having zero mean value. When a detectable substance is accumulated on sensing crystal oscillator 110 an amplitude of comparator tracking signal 320 can be expected to increase, indicative of an amplitude of the jitter changing in one direction only. Accordingly, a mean value of the jitter is no longer zero. Detecting an amplitude of comparator tracking signal 320 provides an indication of a substance adhering to sensing crystal oscillator 110.

Jitter that can be sensed when use of sensor 100 can be dependent on a plurality of factors including on a random noise jitter of sensing crystal oscillator 110 and a mass and temperature of molecules of interest in an environment which adhere to an active surface of sensing crystal oscillator 110. An amplitude (magnitude) of a phase differential change within an on time sensing period of sensor 100 can be a function of a density of molecules being detected for in an environment. A frequency of a phase differential change within an on time sensing period of sensor 100 can be a function of a mass and temperature of molecules being detected for in an environment. Accordingly, a phase analyzer 130 can be utilized for determining a density of molecules adhering to sensing crystal oscillator 110 as well as a mass and temperature of molecules adhering to sensing crystal oscillator 110. In one embodiment, phase analyzer 130 can include a lookup table correlating molecule mass with substance type. Sensor 100 can utilize such lookup table for determining substance type based on molecule mass. Where phase analyzer 130 determines parameters utilizing jitter frequency and amplitude, phase analyzer 130 can process a raw signal output of sensing crystal oscillator 110 and reference crystal oscillator 120 without use of a phase comparator tracking signal 320 and without use of low pass filter 150 (e.g., raw signals output by sensing crystal oscillator 110 and reference crystal oscillator 120 can be routed to digital signal processor 160 which can digitize the signals and phase comparator 140 and low pass filter 150 can be bypassed).

In one embodiment an output of phase comparator 140 used for substance detection can be used as a control to control phase locking of sensing crystal oscillator 110 and reference crystal oscillator 120. In another embodiment a feedback path separate from phase analyzer 130 can be used for phase lock control. In the embodiment of FIG. 3, an output of phase comparator 140 as filtered by low pass filter 150 can be input to sensing crystal oscillator 110 for phase lock control. In the embodiment of FIG. 3 sensing crystal oscillator 110 is provided by a voltage controlled oscillator having a frequency controlled by an output of phase comparator 140 as filtered by low pass filter 150. In one example a voltage applied to sensing crystal oscillator 110 can be varied to achieve phase lock (a common output frequency for the sensing crystal oscillator 110 and the reference crystal oscillator 120).

In one embodiment sensor 100 can be provided so that sensing crystal oscillator 110 and reference crystal oscillator 120 oscillate at a common frequency. For providing a phase lock for sensor 100 so that sensing crystal oscillator 110 and reference crystal oscillator 120 oscillate at a common frequency, various controls can be provided. For example, sensing crystal oscillator 110 and reference crystal oscillator 120 can be regulated to be maintained at certain respective first and second temperatures. In one embodiment, the first and second temperatures are common temperatures. In another embodiment, the first and second temperatures are different temperatures. Other controls in an operating environment of sensing crystal oscillator 110 and reference crystal oscillator 120 can be provided, e.g. humidity control. The frequency of oscillation can be maintained to be in common between the sensing crystal oscillator 110 and the reference crystal oscillator 120. The sensing crystal oscillator 110 and the reference crystal oscillator 120 can be configured to exhibit a certain baseline phase shift. The baseline phase shift can be set to any phase, e.g. 0 degrees to 360 degrees. A convenient baseline phase shift is 180 degrees or 90 degrees, or 0 degrees. In one embodiment the output of low pass filter 150 can be used for providing a phase lock for sensor so that oscillation 110 is oscillator 120 oscillation at common frequency. The baseline phase difference needed to provide lock is a function of many factors such as temperature, component values, crystal characteristics and other static parameters. In addition, the baseline phase difference can be controlled by a bias voltage signal applied to sensing crystal oscillator 110.

When a substance accumulates on sensing crystal oscillator 110, a phase shift is realized. If a substance continues to accumulate phase shifting will continue over time. However, as a practical matter, a sensitivity of sensing crystal oscillator 110 can diminish over time due to substance build up. In one method for alleviating build up, the oscillator is heated to a high temperature on a periodic basis to burn off the buildup. Thus, sensor 100 in one embodiment can have active sensing stages and inactive "burn off" stages.

In another embodiment, a temperature of sensing crystal oscillator 110 can be regulated so that a rate of accumulation of a substance onto sensing crystal oscillator 110 can correspond to a rate of burn off. More particularly, a temperature of sensing crystal oscillator 110 can be regulated so that a probability of a molecule adhering to a surface of sensing crystal oscillator 110 is approximately equal to a probability of a molecule exiting the surface. In such manner, an intake of a substance can be detected and at the same time oscillator remains perpetually "clean" so that a sensitivity of sensing crystal oscillator 110 remains continually high and further so that "burn off" stages in which sensor 100 is not sensing can be avoided. Exemplary outputs of digital signal processor (DSP) 160 are shown in FIGS. 4 and 5. The output of FIG. 4 indicates the case that sensor 100 is controlled to have burn off periods where a temperature of sensing crystal oscillator 110 is increased to a high level to burn off accumulated substance. FIG. 5 illustrates an exemplary output of sensor where a temperature sensing crystal oscillator 110 is controlled so that a rate of accumulation of a substance detected for corresponds to a rate of removal of the substance. The output in each case is a phase differential of sensing crystal oscillator 110 and reference phase differential 102 relative to a baseline phase differential.

Referring to the output plot of FIG. 4, period 402 is a period prior to activation of sensor 100, period 404 is a period after activation of sensor 100 with no substance in an environment in which sensor is disposed (noise level phase jitter is illustrated by the output), period 406 is a period in which sensor 100 is exposed to an environment having a substance being detected, period 408 is a period after period 406 in which the substance detected during period 406 is no longer present (output level stabilizes), period 410 is a period is which sensor 100 is once again exposed to an environment having a substance detected for (during period 410 the substance is present in greater quantities and hence the rate of change in phase differential from a baseline level is increased), period 412 is another period in which the substance is no longer present, period 414 is a "burn off" period in which sensing crystal oscillator 110 is heated to a high level to burn off accumulated substance, period 416 is a period in which sensor 100 is activated for sensing no substance detected in the environment (noise level, phase jitter is illustrated) and period 418 is a period after deactivation of sensor 100.

Referring to the output plot of FIG. 5 (referring to an implementation wherein a temperature of sensing crystal oscillator 110 controlled so accumulation rate corresponds to removal rate), period 502 is a period prior to activation of sensor 100, period 504 is a period after activation sensor 100 with no substance detected (noise level phase jitter is illustrated by the output), period 506 is a period in which a substance is detected in a first concentration, period 508 is period in which a substance is detected at a second concentration greater than the first concentration (the rate of change in phase differential from a baseline level is increased), period 510 is a period in which a substance is no longer present in an environment (noise level phase jitter is illustrated) and period 512 is a period after which sensor 100 has been deactivated. During the periods 506 through 510, the temperature of the sensing crystal oscillator 110 is being increased periodically, causing the sawtooth nature of the response.

Additional exemplary embodiments of sensor 100 (including details of sensor 100 in various embodiments and of applications and methods involving use of sensor 100 in various embodiments), are set forth in Appendix A entitled "Ultra-Sensitive Quartz Crystal Monitor (QCM)," Appendix B entitled "Quartz Crystal Monitor for the Detection of ppb Concentrations or Explosives," and Appendix C entitled "Electronic Nose For Explosive Detection" of U.S. Patent Application No. 61/696,389, each of which is incorporated herein and forms part of the present disclosure. Each of referenced Appendix A, Appendix B and Appendix C is incorporated herein by way of being appended hereto and by way of forming part of the disclosure of U.S. Patent Application No. 61/696,389 filed Sep. 4, 2012 entitled, "SENSOR FOR SENSING SUBSTANCES IN AN ENVIRONMENT" which is incorporated herein by reference in its entirety.

A small sample of apparatus systems and methods and apparatus that are described herein is as follows:

A1. A sensor comprising: a sensing crystal oscillator; a reference crystal oscillator, wherein the sensing crystal oscillator and the reference crystal oscillator are arranged in a phase locked loop so that sensing crystal oscillator and the reference crystal oscillator oscillate at a common frequency; and a phase analyzer responsive to a change in phase between an output of the sensing crystal oscillator and an output of the reference crystal oscillator, wherein a change in phase between an output of the sensing crystal oscillator and an output of the reference crystal oscillator indicates a presence of a substance in an environment. A2. The sensor of A1, wherein a temperature of the sensing crystal oscillator is regulated so that a rate of adding material to the sensing crystal oscillator is equal to a rate of removal of material from the crystal oscillator. A3. The sensor of A1, wherein the phase analyzer comprises a phase comparator. A4. The sensor of A1, wherein the sensing crystal oscillator and the reference crystal oscillator are housed in a temperature controlled environment. A5. The sensor of A1, wherein temperatures of the sensing crystal oscillator and the reference crystal oscillator are regulated to be maintained at first and second regulated temperatures.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than or greater than the mentioned certain number of elements. Also, while a number of particular embodiments have been described, it will be understood that features and aspects that have been described with reference to each particular embodiment can be used with each remaining particularly described embodiment.

I claim:

1. A sensor comprising:
a sensing crystal oscillator;
a reference crystal oscillator, wherein the sensing crystal oscillator and the reference crystal oscillator are arranged in a phase locked loop so that sensing crystal oscillator and the reference crystal oscillator oscillate at a common frequency; and a phase analyzer responsive to a change in phase between an output of the sensing crystal oscillator and an output of the reference crystal oscillator, wherein a change in phase between an output of the sensing crystal oscillator and an output of the reference crystal oscillator indicates a presence of a substance in an environment.

2. The sensor of claim 1, wherein a temperature of the sensing crystal oscillator is regulated so that a rate of adding material to the sensing crystal oscillator is equal to a rate of removal of material from the sensing crystal oscillator.

3. The sensor of claim 1, wherein the phase analyzer comprises a phase comparator.

4. The sensor of claim 1, wherein the sensing crystal oscillator and the reference crystal oscillator are housed in a temperature controlled environment.

5. The sensor of claim 1, wherein temperatures of the sensing crystal oscillator and the reference crystal oscillator are regulated to be maintained at first and second regulated temperatures.

6. The sensor of claim 1, wherein the change in phase between an output of the sensing crystal oscillator and an output of the reference crystal oscillator is provided by a change in phase differential between an output of the sensing crystal oscillator and an output of the reference crystal oscillator.

7. The sensor of claim 1, wherein the sensing crystal oscillator is coated with an attractant.

8. The sensor of claim 1, wherein the sensing crystal oscillator is coated with an attractant provided by an acid.

9. The sensor of claim 1, wherein the sensing crystal oscillator is adapted to encourage accumulation of a substance on the sensing crystal oscillator.

10. The sensor of claim 1, wherein the phase analyzer in being responsive to change in phase between an output of the sensing crystal oscillator and an output of the reference crystal oscillator is responsive to a change in phase differential between an output of the sensing crystal oscillator and an output of the reference crystal oscillator.

11. The sensor of claim 1, wherein the sensor provides a tracking signal having an amplitude that changes with changes in a phase differential between an output of the sensing crystal oscillator and an output of the reference crystal oscillator.

12. The sensor of claim 1, wherein the sensor provides a signal having a pulse length that changes with changes in a phase differential between an output of the sensing crystal oscillator and an output of the reference crystal oscillator.

13. The sensor of claim 1, wherein the sensor produces jitter that increases in amplitude when a substance is sensed.

14. The sensor of claim 1, wherein the sensing crystal oscillator and the reference crystal oscillator operate at a frequency of about 6 MHz.

15. The sensor of claim 1, wherein a period of oscillation of the sensing crystal oscillator is proportional to a mass of molecules adhering to a surface of the sensing crystal oscillator.

16. The sensor of claim 1, wherein the sensor is operative to detect an explosive in an environment.

17. The sensor of claim 1, wherein the sensor is operative to determine a type of substance in an environment.

18. The sensor of claim 1, wherein the sensor is operative to determine a type of substance in an environment using a lookup table correlating molecule mass with substance type.

19. The sensor of claim 1, wherein the sensor includes a heated holder on which the sensing crystal oscillator is mounted.

20. The sensor of claim 1, wherein the sensor is operative to direct air in proximity with sensor electronics of the sensor.

* * * * *